United States Patent [19]

Vasconcelos et al.

[11] Patent Number: 5,104,397
[45] Date of Patent: Apr. 14, 1992

[54] MULTI-POSITION LATCHING MECHANISM FOR FORCEPS

[75] Inventors: Gilson S. Vasconcelos, New Bedford; John A. Santangelo, East Freetown, both of Mass.

[73] Assignee: Codman & Shurtleff, Inc., Randolph, Mass.

[21] Appl. No.: 338,801

[22] Filed: Apr. 14, 1989

[51] Int. Cl.[5] .............................. A61B 17/28
[52] U.S. Cl. .................... 606/206; 606/208; 81/322; 81/313
[58] Field of Search .............. 606/205–208, 606/210, 211; 81/313, 314, 316, 322, 323, 336, 337, 338

[56] References Cited

U.S. PATENT DOCUMENTS

| | | |
|---|---|---|
| 1,832,879 | 11/1931 | Ruskin .......................... 606/208 |
| 2,178,391 | 10/1939 | Curtiss . | 
| 3,326,216 | 6/1967 | Wood .......................... 606/207 X |
| 3,393,680 | 7/1968 | Curutchet . |
| 3,921,640 | 11/1975 | Freeborn ...................... 606/207 X |
| 4,462,404 | 7/1984 | Schwarz et al. .............. 606/206 |
| 4,602,631 | 7/1986 | Fanstan . |
| 4,777,950 | 10/1988 | Kees, Jr. . |
| 4,823,792 | 4/1989 | Dulebohn et al. ........... 606/208 X |

OTHER PUBLICATIONS

Codman & Shurtless, Inc., 1965 Catalog, p. 86 Boston, Mass. 02125.

*Primary Examiner*—Mickey Yu

[57] ABSTRACT

A latching mechanism for forceps including first latch portion on one forcep handle and a second latch portion on the other forceps handle and a bias spring for placing the handles, and thus the jaws, in a first predetermined spacing. The first latch portion has a cam surface, a shelf and a slot. The second latch portion has a transverse projection which engages the cam surface as the handles close and then engages the shelf and upon further closing of the handles and then springs through the slot to disengage the latching mechanism and return the handles to the original position controlled by the bias spring. The first position allows a surgical assistant to load an aneurysm clip into the jaws of the forceps. The second predetermined position allows the surgical assistant to partially close the handles sufficient to hold the aneurysm clip firmly in place. The surgeon then takes the forcep and inserts the aneurysm clip by further closing the handles and releases the latching mechanism by relaxing the grip.

7 Claims, 3 Drawing Sheets

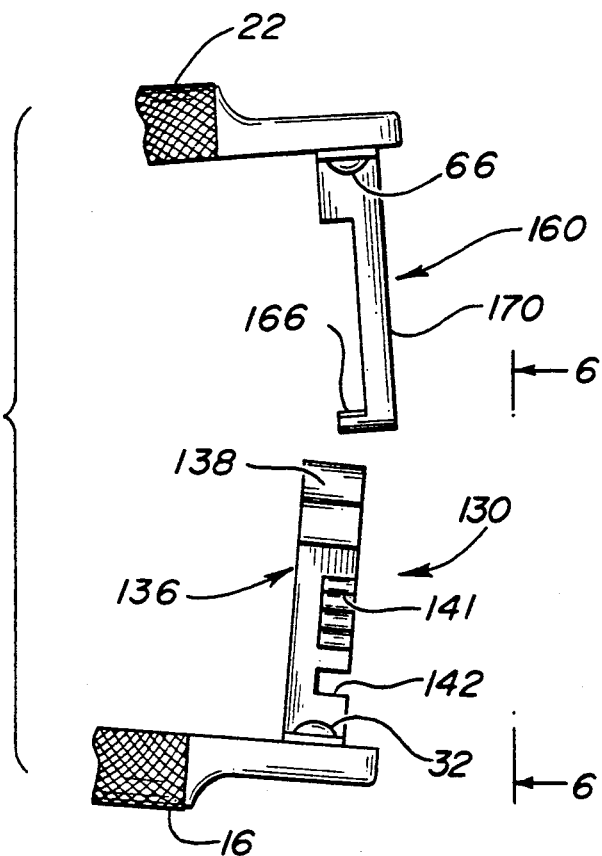
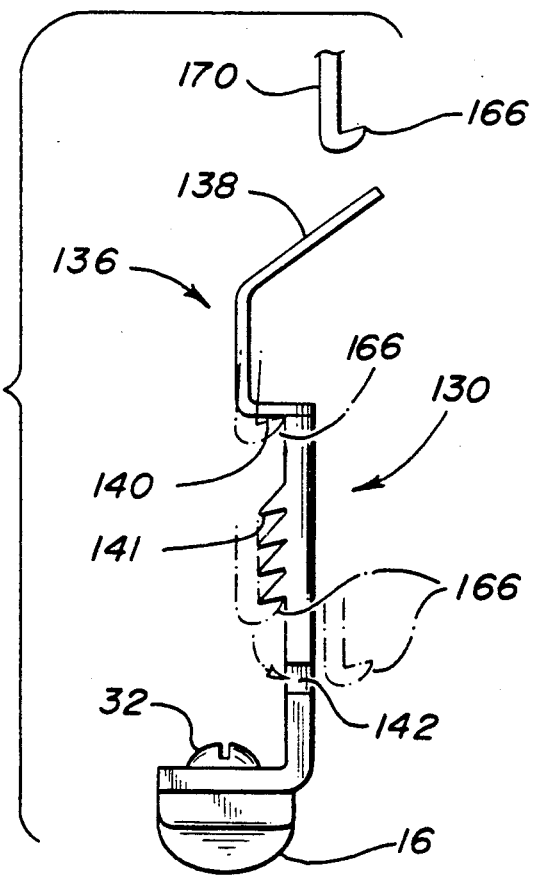

MULTI-POSITION LATCHING MECHANISM FOR FORCEPS

FIELD OF THE INVENTION

The present invention relates to a latching mechanism for a forceps-type surgical instrument and, more particularly, to a multi-position latching mechanism for an aneurysm clip applying forceps. The latching mechanism holds the forceps jaws at various predetermined spacings to facilitate the loading of clips into the jaws and the placement of clips on the anatomy about the surgical site.

BACKGROUND OF THE INVENTION

Forceps are used to place a variety of clips on the anatomy during surgery. A variety of clips usually hemostatic clips are applied with forceps. One type of hemostatic clip of particular interest is an aneurysm clip. One type of aneurysm clip is shown in U.S. Pat. No. 4,777,950.

Hemostatic clips, including aneurysm clips, are applied to blood vessels in various ways to close or strengthen a blood vessel during or after surgery. The jaws of a forceps are usually designed to receive a particular type of clip. A clip is loaded into the jaws by the surgical assistant and then handed to the surgeon who inserts the clip into the surgical site.

To load a clip into the jaws the surgical assistant opens the jaws and places the clip between the jaws manually and then closes the jaws enough to hold the clip in place so that it will not fall out during insertion. It is, however, important that the jaws not be closed too much so as to start to open the clip since that might interfere with the proper insertion of the clip.

One way of setting the jaws at a predetermined position is to use two projections from the inside of each handle of the forceps which overlap and interlock as is shown for example in U.S. Pat. No. 3,393,680. Although this is a satisfactory lock for some applications, it is not particularly well suited to applying an aneurysm clip. A leaf spring extending between the insides of the two opposing handles of the forceps is used to bias the handles apart so that when the lock is disengaged the forceps handles will open a predetermined amount thus opening the jaws of the corresponding predetermined amount.

Another kind of forceps locking mechanism is shown in U.S. Pat. No. 4,462,404. This forceps locking mechanism can be used to place the jaws at multiple positions. A leaf spring attached to the inside of one forceps handle extends across to the inside of the other forceps handle and engages a complex latch which is affixed to the inside of the opposing handle. Although this device works satisfactorily, it is complicated and has variety of parts which must be separately assembled to the forceps. Care must be taken with this kind of latch mechanism to make sure that it does not become damaged and misaligned during cleaning and sterilization of the forceps.

It would be useful to have a latching device of simpler design which could be used to set the jaws of the forcep in a variety predetermined spaced apart positions so that the surgical assistant could first load the clip into the jaws and then firmly set the clip into position without activating the clip. This would allow the surgical assistant to quickly load the clip and hand the instrument to the surgeon who could easily insert the clip into the surgical site. It would also be useful to have the latch recycled to its initial position as the surgeon releases his grasp on the forceps to further facilitate the loading of the next clip by the surgical assistant or repositioning or removal of a clip just placed without withdrawing the applier from the surgical site. Quick, one hand recycling of the latch mechanism would be very useful in repositioning or removing a clip.

SUMMARY OF THE INVENTION

The present invention relates to a latching mechanism for a forceps type surgical instrument.

The forceps has first and second members, each having a jaw disposed in opposing relationship on the distal end portion and each having a handle disposed in opposing relationship on the proximal end portion. The members are pivotably connected together so that as the handles are closed toward one another, the jaws close toward one another. The latching mechanism includes a first latch portion extending from the first member with a resiliently flexible free end and having an engaging surface. A second latch portion on the second member includes a free end adapted for engaging the engaging surface of the first latch portion. The first latch portion free end and the second latch portion are biased into engagement. A stop formation, preferably a shelf, is formed on the first latch portion engaging surface for receiving and holding at least a portion of the free end of the second latch portion when the handles are in a first predetermined position. The latching mechanism includes a release for moving the free end of the second latch portion out of engagement with the engaging surface upon further closing of the handles toward one another. There is also a means for biasing the handles apart.

In the preferred embodiment, the second latch portion includes a transverse extension adapted to engage the engaging surface of the first latch portion.

The second latch portion transverse extension may include a cross bar and connecting means connecting the cross bar to the remainder of the second latch portion so that the cross bar is spaced longitudinally at the free end of the second latch portion.

The means for biasing the two handles apart may include an extension from each latch portion extending proximally beyond the proximal ends of the handles with the proximal ends of the extensions are releaseably connected together.

Alternatively, the biasing means may extend distally from the latch portions between the two members and may include leaf springs which are releaseably connected together by a slot and tab on the respective ends of the leaf springs.

The first latch portion engaging surface may include a cam surface for directing the free end of the second latch portion and a step for holding the free end of the second latch portion. The engaging surface may also include a release, which in the preferred embodiment includes a slot extending transversely into the side of the first latch portion to receive at least a part of the free end of the second latch portion so that as the handles move toward one another, the free end of the second latch portion moves into and through the slot.

The first and second latch portions are resiliently flexible in the same plane of motion and the plane may be oriented with respect to the plane of motion of the handles at a variety of convenient angles.

In an alternative embodiment, the biasing means can be a compression spring placed between the members of the forceps to bias the handles apart.

The latch portions are preferably made of spring steel and preferably attached to the proximal portion of the inside of each handle.

As the latching mechanism moves among its various positions, audible and tactile signals inform the user of the operation of the latching mechanism.

These and other features and advantages of the present invention will become more apparent from the following detailed description of the preferred embodiment taken in conjunction with the following drawings.

BRIEF DESCRIPTION OF THE DRAWINGS

FIG. 5 shows a partial side elevation of an alternative embodiment of the invention; and, FIG. 6 shows a partial end view of the latching mechanism shown in FIG. 5 taken along line 6—6 in FIG. 5.

DETAILED DESCRIPTION OF THE PREFERRED EMBODIMENTS

Figure 1:
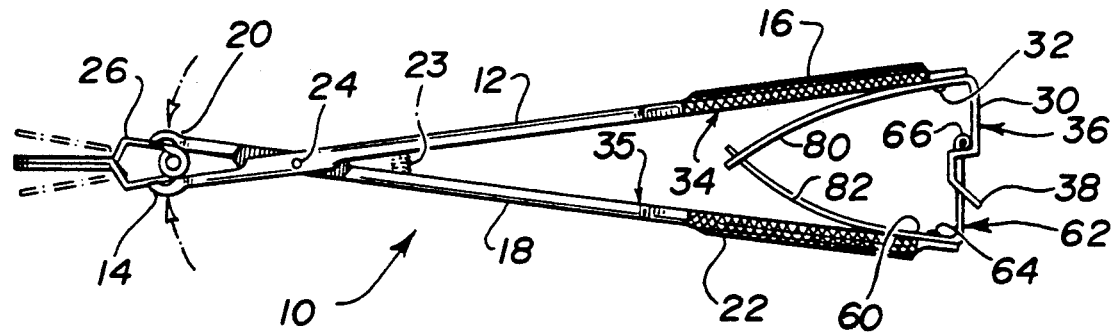
FIG. 1 shows a side elevation of the forceps and latching mechanism of the present invention with an aneurysm clip placed in the jaws with phantom lines indicating that as the jaws close the clip opens.

Referring now to FIG. 1 there is shown a forceps 10 having a first member 12 with a jaw 14 on its distal end and a handle 16 on its proximal end and a second member 18 with a jaw 20 on its distal end and a handle 22 on its proximal end. Members 12 and 18 are pivotably connected together at pivot point 24.

Jaws 14 and 20 are especially configured to hold an aneurysm clip 26. First latch portion 30 is attached by suitable means, preferably screw 32, to the inside 34 of the distal portion of handle 16. Second latch portion 60 is attached by suitable means, preferably screw 64, to the inside 35 of the distal portion of handle 22

First and second latch portions 30 and 60 are preferably a piece of flat spring steal but may be made in any convenient shape or of any suitable resilient material so that first and second latch portions 30 and 60 may be flexibly resilient in the same plane and preferably in the plane of motion of handles 16 and 22 (see FIG. 1) or in a plane perpendicular to the plane of motion of the handles (see FIGS. 5 and 6).

It will be noted that handles 16 and 22 may be offset from the body of members 12 and 18 to form what is known in the surgical instrument vernacular as a bayonet style forceps such that the plane in which jaws 14 and 20 move is laterally offset from the plane in which handles 16 and 22 move. This offset bayonet design is convenient for such instruments but is not essential.

Figure 2:
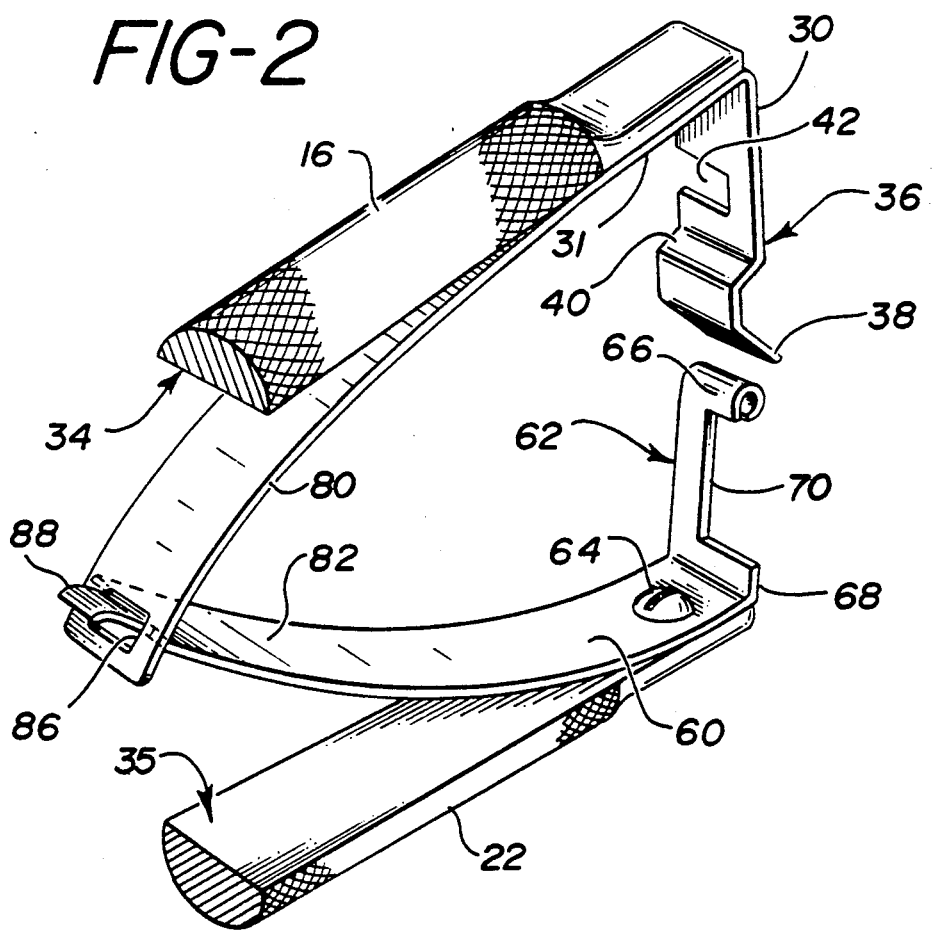
FIG. 2 shows a partial perspective of the latching mechanism.

First latch portion 30 is preferably L-shaped with the base 31 of the L attached to the proximal end of handle 16 and the shaft of the L including a specially configured engaging surface 36 which projects toward handle 22. Engaging surface 36 includes a cam surface 38 which is shown in FIG. 2 and is preferably a straight ramp at the free end of first latch portion 30. Cam surface 38 of engaging surface 36 can be any convenient shape so as to engage and deflect the confronting surface of second latch portion 60 which will be explained later in the application.

Engaging surface 36 also includes a shelf 40 which, in this preferred embodiment, is generally at right angles to the adjacent surface of first latch portion 30. Shelf 40 may form any convenient angle with the adjacent surface of first latch portion 30 sufficient to hold the free end 62 of second portion 60 of the latch mechanism, and hence handles 16 and 22, in a first predetermined position. Shelf 40 provides a formation for stopping free end 62 of second latch portion 60.

A slot 42 extends into one side of engaging surface 36 of first latch portion 30 and is located a predetermined distance above shelf 40. Slot 42 provides a means for releasing the free end 62 of second latch portion 60 under the resilient forces experienced by latch portions 30 and 60 as handles 16 and 22 close toward one another from the position where free end 62 of second latch portion 60 stops on shelf 40. Slot 42 can be on either side of first latch portion 30 or may even be placed in the middle of first latch portion 30 so long as free end 62 of second latch portion 60 can be released from shelf 40 by passing through slot 42.

Second latch portion 60 is affixed along the inside surface 35 of member 18 preferably at the proximal portion of handle 22 by means of screw 64. Second latch portion 60 is preferably L-shaped with the base 61 of the L being attached to member 22 and the shaft of the L projecting toward first latch portion 30. The free end 62 of second latch portion 60 includes a transverse projection 66. Transverse projection 66 may be any convenient shape but is preferably an L-shaped projection extending from a proximal portion 68 of second latch portion 60 with the crossbar portion of the L-shaped projection corresponding to transverse projection 66 and the shaft 70 of the L-shaped projection extending from a proximal portion 68 of second latch portion 60. Transverse projection 66 may extend from either side of second latch portion 60 and can be at any convenient angle so long as it interacts properly with cam surface 38 and shelf 40 of first latch portion 30.

Transverse projection 66 need not be L-shaped but may be any convenient shape so long as transverse projection 66 is held in a position that will permit it to interact with engaging surface 36 and to easily enter shelf 40 and slot 42 when necessary. For example, shaft 70 could be C-shaped instead of straight or any other shape that provides a convenient connection between transverse projection 66 and proximal portion 68 of second latch portion 60.

The handles 16 and 22 are biased apart preferably by means of leaf spring projections 80 and 82 extending distally from latch portions 30 and 60. Leaf springs 80 and 82 are preferably are made of spring steel and are made integral with their corresponding latch portions 30 and 60. Leaf spring 80 includes a slot 86 near its end and leaf spring 82 includes a tab 88 near its end. Slot 86 and tab 88 connect together to hold members 80 and 82 together to provide a spring force to bias handles 16 and 22 apart a predetermined amount. Alternatively, leaf springs 80 and 82 may extend proximally of handles 16 and 22.

Handles 16 and 22 could be biased apart by placing one or more compression or torsion springs 23 between members 12 preferably at a point close to pivot point 24 and also preferably obscured by the pivot point of forceps 10.

The operation of the latch mechanism in the present invention will now be described.

Figure 3:
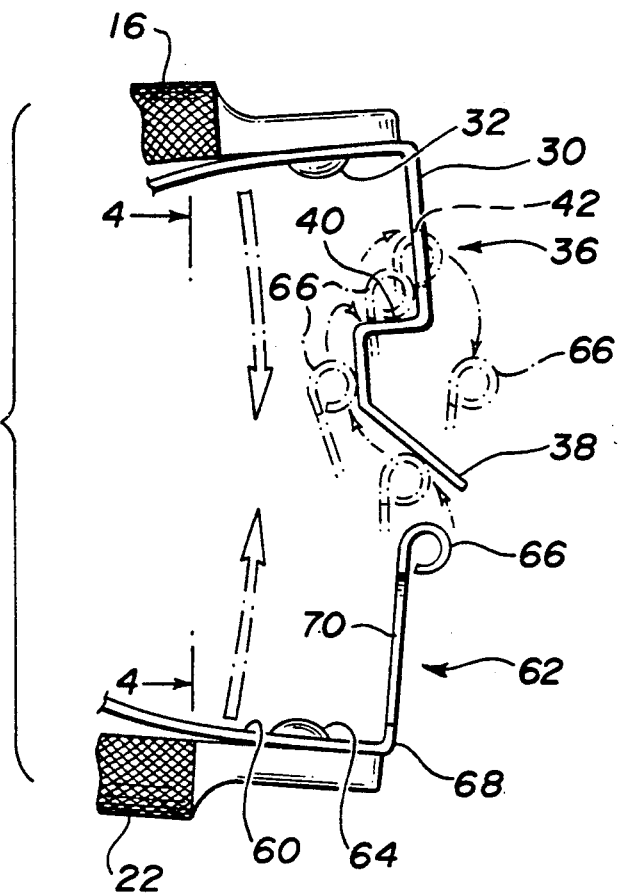
FIG. 3 shows a partial side elevation of the latching mechanism.
Figure 4:
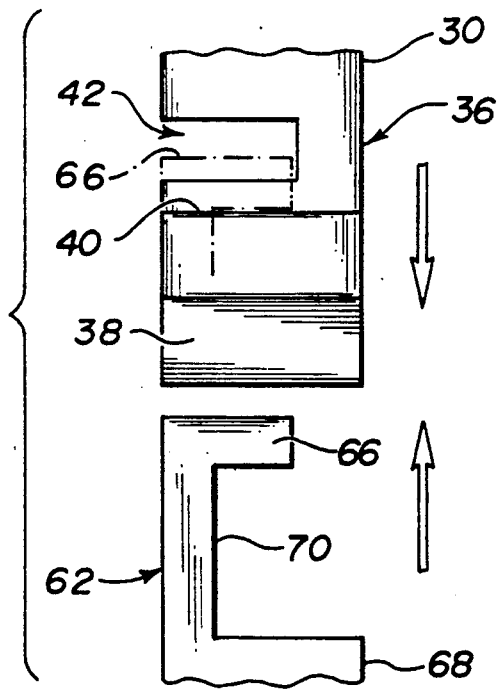
FIG. 4 is a partial end view of the latching mechanism shown in FIG. 3.

One can see from FIG. 2 that leaf spring members 80 and 82 will bias handles 16 and 22 and, thus, jaws 14 and 20 apart a predetermined distance so that latch portions 30 and 60 are not in contact and so that the surgical assistant can place aneurysm clip 26 within jaws 14,20. The surgical assistant then proceeds to close handles 16 and 22 together to engage latch portions 30 and 60. Referring now to FIG. 3, one will see that as handles 16 and 22 are closed together transverse projection 66 of second latch portion 60 is aligned to engage cam surface 38. The resiliency of latch portions 30 and 60 will cause one or both of latch portions 30 and 60 to deflect in a plane generally parallel to the plane of motion of the handles 16 and 22 causing transverse projection 66 to ride along cam surface 38 and then further along engaging surface 36 of first latch portion 30 until the resiliency of latch portions 30 and 60 cause transverse projection 66 to move onto shelf 40. An audible and tactile signal will be generated when this occurs.

With transverse projection 66 stopped on shelf 40, aneurysm clip 26 is firmly fixed in jaws 14 and 20 without activating aneurysm clip 26. The surgical assistant may then hand the forceps to the surgeon who inserts forceps 10 and aneurysm clip 26 into the surgical field. As the surgeon further closes handles 16 and 22 together, the jaws of clip 26 will open so they may encompass the anatomy of interest. As the surgeon closes handles 16 and 22 further, transverse projection 66 will slide resiliently further along engaging surface 36 above shelf 40 until transverse projection 66 is aligned with and springs through slot 42. The resilient action of latch portions 30 and 60 will then separate latch portions 30 and 60 so that leaf springs 80 and 82 may return handles 16 and 22 to their original position as the surgeon relaxes his grip to open jaws 14 and 20 and set clip 26 on the anatomy of interest.

Those skilled in the art will recognize that the initial spacing of the jaws can be properly controlled by adjusting leaf spring members 80 and 82. This is important because these parts can become bent and misaligned during cleaning and sterilization, but it is easy to realign them to allow the latch mechanism to work properly.

If, after setting clip 26, the surgeon wishes to reposition or even withdraw it, he can easily do so without removing forceps 10 from the incision. Open jaws 14 and 20 can be placed about clip 26 and closed until transverse projection 66 engages shelf 40 indicating to the surgeon that clip 26 is secured in jaws 14 and 20. The surgeon then closes handles 16 and 20 to open jaws of clip 26 for repositioning. If the surgeon wishes to completely remove clip 26, one may follow the above steps for repositioning and continue by withdrawing jaws of clip 26 away from the anatomy about which they were positioned. One then closes handles 16, 18 further to thus recycle transverse projection 66 through slot 42 and then relaxes one's grip to close clips 26. One then partially closes handles 16 and 18 to engage transverse projection 66 on shelf 40. The surgeon, knowing that clip 26 is firmly held in jaws 14, 20 and that clip 26 is closed, can withdraw clip 26 with its jaws closed so as to avoid damage to the surrounding anatomy during withdrawal.

Referring now to FIGS. 5 and 6 there is shown an alternative embodiment of the present invention. First latch portion 130 is attached to the distal portion of handle 16 and extends toward handle 18 and includes an engaging surface 136 including a cam surface 138, a shelf 140, a plurality of retaining steps 141 and a slot 142.

Second latch portion 160 is attached to a proximal portion of handle 18 and extends toward handle 16 and includes a generally L-shaped portion having a shaft 170 and a transverse projection 166.

First and second latch portions 130 and 160 are made of spring steel and are resiliently flexible in the same plane, which in the embodiment of FIGS. 5 and 6, is shown perpendicular to the plane of motion of handles 16 and 18. The plane of resilient flexibility of latch portions 130 and 160 can be set at any convenient angle to the plane of motion of handles 16 and 18 by rotating latch portions 130 and 160 about their attachment screws 32 and 64.

Handles 16 and 18 are held in a first predetermined position by leaf springs similar to leaf springs 80 and 82 of the embodiment shown in FIG. 1 or by means of a compression spring 23 like that shown in FIG. 1.

The operation of this embodiment will now be explained. With handles 16 and 18 separated under the influence of the biasing springs (not shown) the surgical assistant can insert an aneurysm clip 26 in the jaws of the forceps as was done with the embodiment of FIG. 1. The surgical assistant then closes handles 16 and 18 together so that transverse projection 166 contacts cam surface 138 deflecting latch portions 130 and 160 as the contact continues. Transverse projection 166 will engage shelf 140 as the closing of handles 16 and 18 continues. The surgical assistant may then hand the forceps to the surgeon knowing that clip 26 is firmly held in the jaws of the forceps. The variety of steps 141 are provided so that a number of fixed positions of the latch mechanism and correspondingly of the forceps jaws may be set. As the surgeon further closes handles 16 and 18 together transverse projection 166 will travel toward and then spring through slot 142 under the influence of the resilient flexibility of latch portions 130 and 160, thus releasing the latch mechanism and allowing the surgeon to release his grip on handles 16 and 18 to recycle the latch.

The present invention has been described in conjunction with the preferred embodiments. Those skilled in the art will appreciate that many modifications and changes may be made to the preferred embodiments without departing from the present invention. It is, therefore, not intended to limit the present invention except to set forth in the appended claims.

We claim:

1. In a forceps-types surgical instrument having first and second members each having a jaw disposed in opposing relationship on a distal portion thereof and each having a handle disposed in opposing relationship on a proximal portion thereof said members pivotably connected together so that as said handles are closed toward one another said jaws close toward one another, the improvement comprising:

a first resilient latch portion attached adjacent the proximal end portion of said first member and having an engaging surface, resiliently flexible in a plane said engaging surface including;

a generally planar cam surface at its free end aligned at an angle to the direction of closure of said handles; and, a stop formation spaced from said free end of said engaging surface;

a second resilient latch portion attached adjacent the proximal portion of said second member, said second latch portion including a projection at its free end extending transversely therefrom and adapted to deflect against said cam surface and to be received and resiliently held on said stop formation against said engaging surface;

when said handles are in a second predetermined position;

a slot in said first latch portion engaging surface extending from a side of said latch portion transversely thereinto for permitting said projection at said free end of said second resilient latch portion to resiliently move through said slot out of engagement with said engaging surface upon further movement of said handles toward one another; and, biasing means for biasing said handles apart at a first predetermined position integral with at least a part of one of said first and second latching member.

2. The instrument of claim 1 wherein said biasing means includes a further portion of said latch portions, integral therewith and extending distally between said handles;

the ends of said further portions of said latch portions releasably connected together.

3. The instrument of claim 1 further including means for providing a signal indicating the movement of said latching mechanism into said predetermined positions.

4. The instrument of claim 1 wherein said biasing means includes at least one compression spring mounted between said members to bias said handles apart.

5. The instrument of claim 1 wherein
said stop formation and said slot being separated by a predetermined distance to allow said handles to close a predetermined amount from said first position before the projection at the free end of said second latch portion passes resiliently through said slot to disengage said latching mechanism.

6. The instrument of claim 1 wherein said stop formation includes a shelf.

7. The instrument of claim 1 wherein said stop formation includes a hook.

* * * * *